United States Patent
Bosc et al.

(10) Patent No.: US 8,703,790 B2
(45) Date of Patent: Apr. 22, 2014

(54) BIS [O-(14-BENZOYLACONINE-8-YL)] ESTERS

(75) Inventors: Jean-Jacques Bosc, Pompignac (FR); Christian Jarry, Artigues Pres de Bordeaux (FR); Ainura Chodoeva, Bordeaux (FR); Jean Guillon, Pessac (FR); Isabelle Forfar, Merignac (FR); Jacques Robert, Bordeaux (FR)

(73) Assignee: Universite Victor Segalen Bordeaux 2, Bordeau Cedex (FR)

( * ) Notice: Subject to any disclaimer, the term of this patent is extended or adjusted under 35 U.S.C. 154(b) by 265 days.

(21) Appl. No.: 13/130,324

(22) PCT Filed: Nov. 26, 2009

(86) PCT No.: PCT/EP2009/065912
§ 371 (c)(1),
(2), (4) Date: Aug. 25, 2011

(87) PCT Pub. No.: WO2010/063638
PCT Pub. Date: Jun. 10, 2010

(65) Prior Publication Data
US 2011/0301187 A1    Dec. 8, 2011

Related U.S. Application Data

(60) Provisional application No. 61/118,673, filed on Dec. 1, 2008.

(30) Foreign Application Priority Data
Dec. 1, 2008 (EP) ..................................... 08170379

(51) Int. Cl.
A61K 31/439 (2006.01)
C07D 221/22 (2006.01)

(52) U.S. Cl.
USPC ............................................. 514/281; 546/43

(58) Field of Classification Search
USPC ........................................... 514/281; 546/43
See application file for complete search history.

(56) References Cited

PUBLICATIONS

Chodoeva, A. et al.: 8-O-Azeloyl-14-benzoylaconine: A new alkaloid from the roots of Aconitum Karacolicum rapes and its antiproliferative activities. Bioorg. & Medicin. Chem., vol. 13, pp. 6493-6501, 2005.*

Chodoeva et al., "Antitumor activity of semisynthetic derivatives of Aconitum alkaloids." Invest New Drugs, DOI 10.1007/s10637-013-9986-z, Published online Jun. 13, 2013.

\* cited by examiner

*Primary Examiner* — Charanjit Aulakh
(74) *Attorney, Agent, or Firm* — Porzio, Bromberg & Newman, P.C.

(57) ABSTRACT

Novel compounds which are alkaloids related to bis [O-(14-Benzoylaconine-8-YL)]esters.

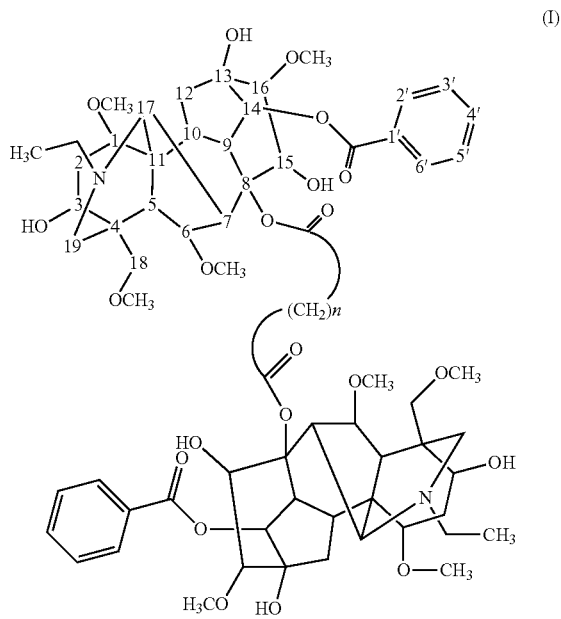

15 Claims, No Drawings

BIS [O-(14-BENZOYLACONINE-8-YL)] ESTERS

Cross Reference to Related Application

This is a National Stage of International Application No. PCT/EP2009/065912, filed 26 Nov. 2009, which claims the benefit of Application No. 08170379.5, filed in Europe on 1 Dec. 2008 and Application No. 61/118,673 filed in the United States on 1 Dec. 2008, the disclosures of which Applications are incorporated by reference herein.

The present invention relates to novel compounds which are alkaloids related to [O-(14-benzoylaconine-8-yl)] moiety.

The invention furthermore concerns a method for producing these compounds, medicaments containing these, and their use in the treatment of cancer.

Despite the wide variety of currently available anticancer drugs, the research and identification of new natural substances extracted from plants with antiproliferative activity remains a priority. Only a small number of available plants have been studied in this respect, and natural biodiversity offers an unlimited field for the discovery of potential anticancer drugs.

In addition, it is to be noticed that numerous plant extracts have currently been used in traditional medicine and their active constituents have never been isolated and identified. Amongst new drugs, natural products and hemisynthetic derivatives of alkaloids have been reported to possess antiproliferative activity.

One example of these natural products is a traditional medicinal plant growing in Kirghiz Republic, which has been preliminary screened. More precisely, this plant belongs to the genus *Aconitum*, family Ranunculaceae and it has been selected for detailed investigation because of its traditional use against cancer in this country for many years. Indeed, the roots of *Aconitum karakolicum* have been used against cancer in some prescriptions of traditional kirghiz medecine.

*Aconitum karakolicum* Rapcs is an herbaceous perennial plant with a tall leafy stem (70-130 cm) bearing violet or blue zygomorphous flowers on long, packed racemes. The underground part of the plant is represented by cone-shaped tubercles measuring 2.0–2.5×0.7-1.0 cm, which grow by sticking to each other side by side. *Aconitum karakolicum* is endemic to Central Asia.

All the parts of *Aconitum* species contain alkaloids of the diterpenoid group. The maximum content in alkaloids has been found in tubercles after the period of vegetation (August-October).

The principal alkaloids identified in this plant are:
- aconitine (0.8-1%), which is well-known to have a strong toxicity and to exhibit both centrally and peripherally effects through preventing the normal closure of sodium channels,
- karakoline (0.05%),
- karakolidine (0.05%),
- zongorine (0.1%), and
- zongoramine (0.01%).

Napelline, aconifine, acetylnapelline and karakonitine have also been identified.

But, it has been found that none of these compounds bear any antiproliferative activity, whereas plant extracts do.

Thus, a work of isolating and identifying the compounds present in extracts of the *A. Karakolicum* roots, which were responsible for this activity, has been undertaken and has been detailed in the publication of A. Chodoeva et al., entitled "8-O-Azeloyl-14-benzoylaconine: A new alkaloid from the roots of *Aconitum karakolicum* Rapcs and its proliferative activities"; *Bioorg. Med. Chem.* (2005), 13, 6493-6501.

Indeed, this publication discloses a novel compound: 8-O-azeloyl-14-benzoylaconine, which has the following structure (1):

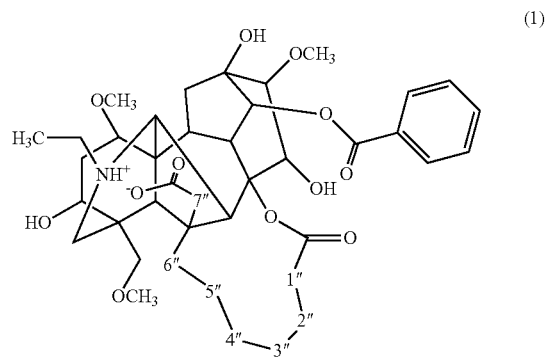

8-O-azeloyl-14-benzoylaconine had never been described in the chemical literature, although several fatty acyl esters of aconine had been previously described in Wie, X.; Xie, H.; Liu, M.; Ge, X., *Heterocycles* (2000), 53, 2027.

Aconine, which is itself devoid of antiproliferative activity, has the following structure (2):

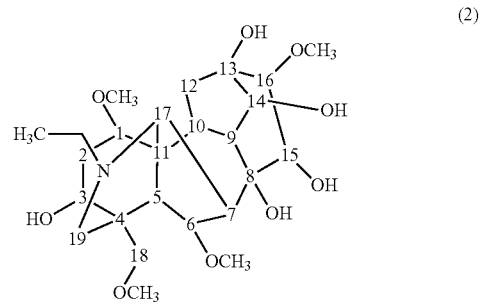

Aconitine, which has been above mentioned, is an aconine derivative and has the following structure (3):

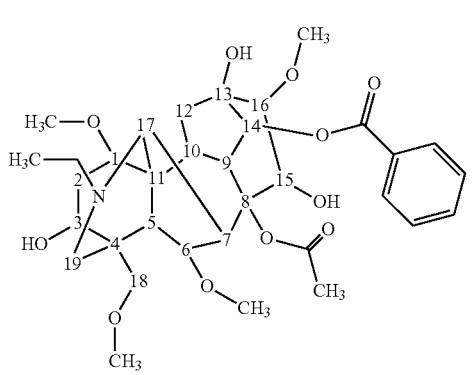
(3)

The 8-O-azeloyl-14-benzoylaconine of general formula $O_{41}H_{59}NO_{13}$ is an aconitine derivative, because it results in fact from the replacement of the acetyl group by an azelaidic acyl moiety on carbon 8 of the aconitine skeleton.

A feature of the compound of 8-O-azeloyl-14-benzoylaconine lies on its zwitterionic structure between the negative charge of the carboxylate function at the extremity of the azelaic acid chain and the positive charge of the quaternary ammonium formed on the nitrogen atom of the heterocycle. Given the length of the azelaic chain, an internal ionic bond between these two moieties could be postulated.

Concerning azelaic acid, it has been shown to be an inhibitor of mitochondrial oxidoreductases in tumour cells (Picardo, M.; Passi, S.; Sirlanni, M. C.; Fiorilli, M.; Russo, G. D.; Cortesi, E.; Barile, G.; Breathnach, A. S.; NazzaroPorro, M.; *Biochem. Pharmacol.* (1985), 34, 1653).

As a consequence, azelaic acid was proposed as a general antitumour agent (Breathnach, A. S., *Med. Hypotheses*, (1999), 52, 221).

Azelaic acid has never been tested in the in vitro screening panel of the NCI, but some experiments have been performed on mouse tumours in vivo, which concluded in the total absence of antitumour activity.

The antiproliferative activity observed for 8-O-azeloyl-14-benzoylaconine cannot therefore be attributed to the activity of its individual constituents.

However, according to the above mentioned publication A. Chodoeva et al., 8-O-azeloyl-14-benzoylaconine has been found responsible for the antiproliferative in vitro activity against three lines of human tumour cells in culture, which were:

HTC-15 (colon cancer),
A549 (lung cancer),
MCF-7 (breast cancer).

Its $IC_{50}$ was about 10-18 µM in these three cell lines, which is in line with the activity of major anticancer drugs belonging to several classes (i.e. antimetabolites, alkylating agents, platinum compounds, topoisomerase inhibitors).

As above mentioned, it is intensively searched for novel compounds exhibiting antiproliferative activity against human tumour cells.

Thus, it was therefore an object of the present invention to improve the design 8-O-azeloyl-14-benzoylaconine, which had revealed very interesting and promising properties against cancer and to provide with novel compounds useful in the cancer chemotherapy.

According to the invention, this object is first of all solved by providing new compounds useful in the cancer chemotherapy, which are alkaloids related to [O-(14-benzoylaconine-8-yl)] moiety.

More precisely, these novel compounds are bis[O-(14-benzoylaconine-8-yl)]esters.

Thus, according to the invention, novel compounds having the following the general structure (I) are provided:

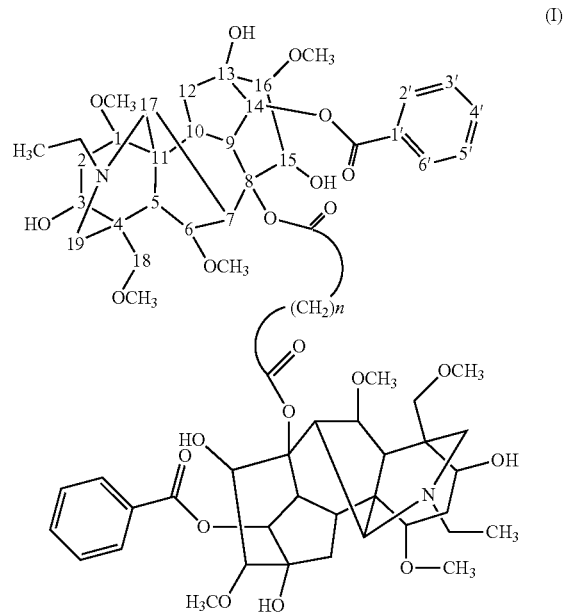
(I)

wherein n is an integer comprised between 0 and 10, preferably between 3 and 10, more preferably between 4 and 8.

Thereby, preferred compounds according to the invention are compounds wherein:
  n is 5, so the compound bis[O-(14-benzoylaconine-8-yl)]-pimelate, (i.e. PDD)
  n is 6, so the compound bis[O-(14-benzoylaconine-8-yl)]-suberate (i.e. SDD),
  n is 7, so the bis[O-(14-benzoylaconine-8-yl)]azelate (i.e. ADD).

Thus, bis[O-(14-benzoylaconine-8-yl)]-pimelate has the following structure:
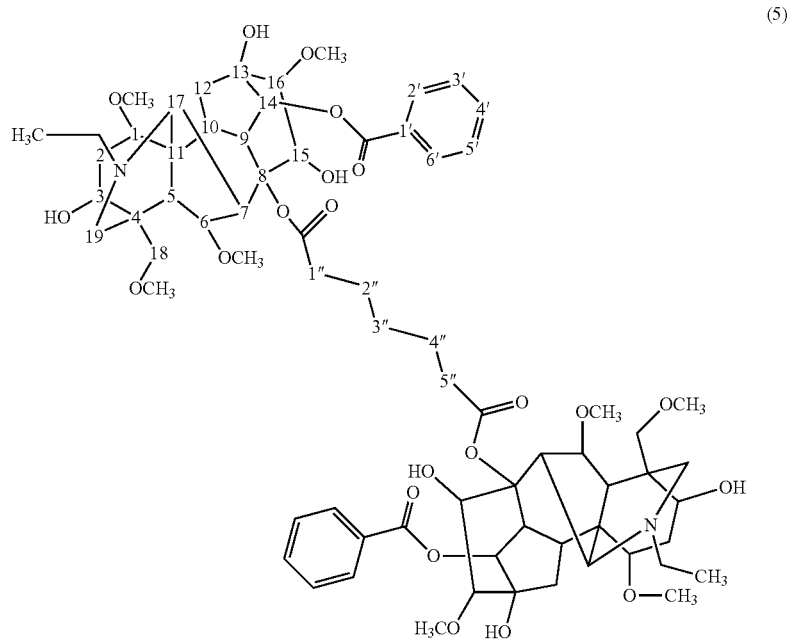
(5)
Thus, bis[O-(14-benzoylaconine-8-yl)]-suberate (i.e. SDD) has the following structure:
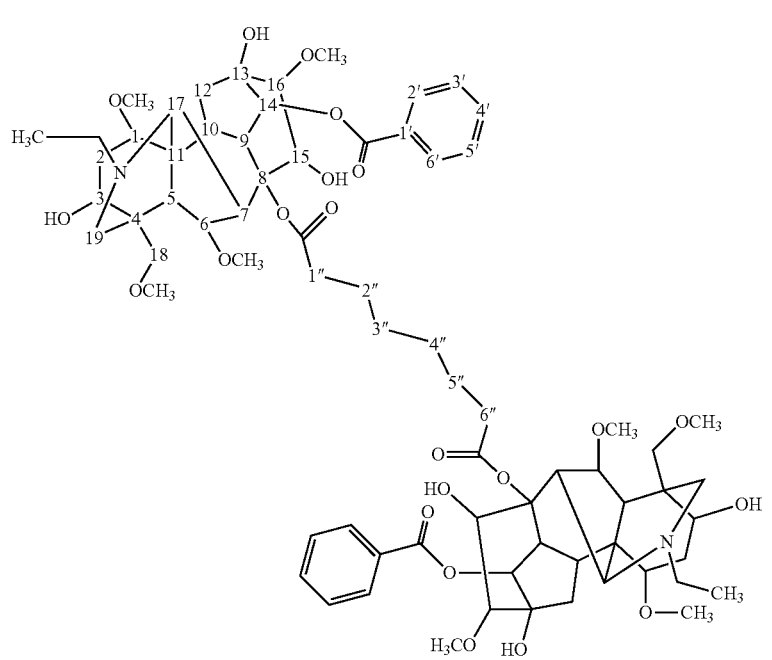
(6)

Thus, bis[O-(14-benzoylaconine-8-yl)]-azelate (i.e. ADD) has the following structure:

(7)

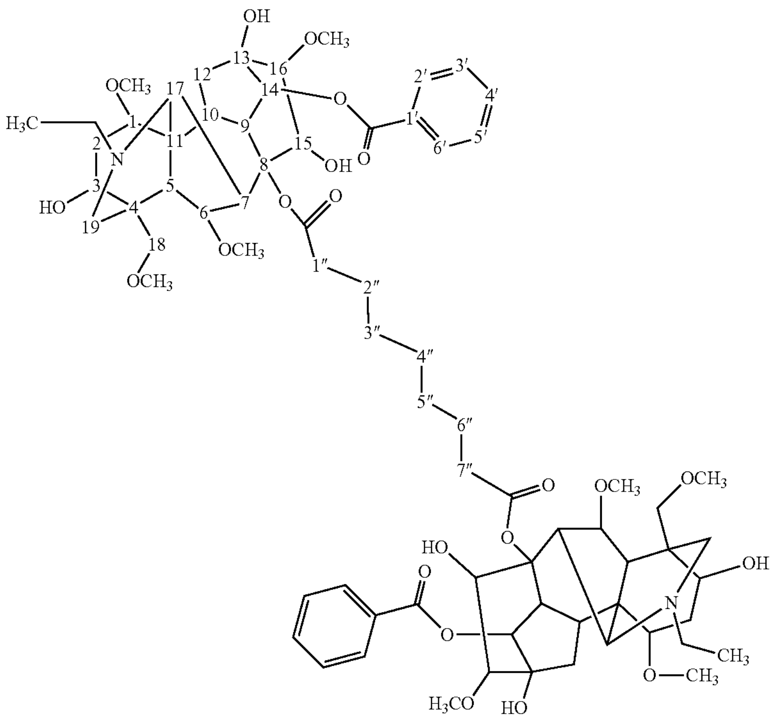

Another object of the present invention relates to a method for producing a compound according to the present invention.

The compounds according to the present invention are obtained by transesterification carried out on the 8-acetyl functionality beared on the aconitine moiety.

The reaction from aconitine is achieved at controlled reaction times and temperature such that it avoids the formation of products of degradation and it optimizes the said reaction of transesterification.

It leads to corresponding mono-[O-(14-benzoylaconine-8-yl)] and bis-[O-(14-benzoylaconine-8-yl)]esters. So, a step of purification is necessary in order to isolate the bis-[O-(14-benzoylaconine-8-yl)]esters according to the present invention.

More precisely, the method for the production of a compound according to the present invention comprises the following steps:

a) stirring aconitine with a dicarboxylic acid at a temperature equal or lower than 80° C. in a solvent such DMF, b) agitating the obtained mixture at room temperature such that the reaction of transesterification is carried out, c) evaporating the solvent under reduced pressure, d) purification of the oily residue obtained at the end of the step c) to isolate the compound according to the present invention.

In preferred embodiments of the invention, the dicarboxylic acid may be selected among the dicarboxylic acids which have a number of carbon atoms comprised between 2 and 12, preferably between 5 and 12, more preferably between 6 and 10.

Most preferably, the dicarboxylic acid may be selected in the group consisting of pimelic acid or suberic acid or azelaic acid.

The stirring of the step a) may be carried out at a temperature comprised between 70° C. and 80° C., and during a time sufficient to carry out the reaction, most preferably during 7 hours.

In a preferred embodiment of the present invention, the agitating of the step b) is carried out during 16 hours in order to optimize the reaction.

More preferably, the evaporating of the solvent of the step c) is carried out at a temperature lower than 70° C.

In a preferred embodiment of the present invention, the purification of the step d) is carried out by a semi-preparative high pressure liquid chromatography.

The conditions of said semi-preparative high pressure liquid chromatography may be the following:

Solvent A: trifluoroacetic acid/water; in proportion of 1/1000;

Solvent B: trifluoroacetic acid/acetonitrile, in proportion of 1/1000.

The elution conditions may consist in an injection of a volume of 0.5 mL; gradient from 25% of B to 100% in 30 min.

The absorbance is monitored at 234 nm.

Another object of the present invention is a pharmaceutical composition which comprises a compound according to the present invention.

The pharmaceutical composition may further comprise a suitable, pharmaceutically acceptable diluent or carrier substance.

In accordance with the invention, the above mentioned pharmaceutical composition can be present in the form of tablets, capsules, droplets, and suppositories, preparations for injection or infusion for a peroral, rectal or parenteral use. Such administration forms and their products are known to the person of skill.

Furthermore, the present invention concerns the use of a compound according to the present invention for the fabrication of a medicament.

More precisely, the present invention concerns the use of a compound according to the invention in which the medicament is used for the treatment of tumour diseases. The tumour diseases may be colon or lung or breast cancer.

The following examples further illustrate the present invention. But, of course, should not be construed as in any way limiting its scope.

First at all, the conditions of different techniques are detailed, which are:

HPLC,
mass spectroscopy, and
NMR.

For all of the Examples the Conditions Used for the HPLC Purification were the Following:

Column used: Ultrasep ES 10, RP 186.0 μm reversed phase, C18 column, 250×10 mm (Bischoff, Germany).

Solvents Used:
A: trifluoroacetic acid/water; in proportion of 1/1000;
B: trifluoroacetic acid/acetonitrile, in proportion of 1/1000;

Elution conditions: injection of a volume of 0.5 mL; gradient from 25% of B to 100% in 30 min.

Absorbance was monitored at 234 nm.

For all of the Examples the Conditions of Mass Spectroscopy were the Following:

High resolution ESI mass measurements were performed on a Applied Biosystems QStar mass spectrometer equipped with an electrospray source in positive mode.

The electrosprayneedle was maintained at 5000 V and operated at room temperature.

Samples were introduced by injection through a 10 μL_sample loop into a 200 μL/min flow of methanol from the LC pump.

$MS^2$ analyses were performed with a collision energy ranging from 30 to 50 and CAD collision gas ranging from 5 to 10.

For all of the Examples the Conditions of Nuclear Magnetic Resonance (NMR) were the Following:

The 1D and 2D NMR experiments were performed on a Bruker DPX400 spectrometer at 400.13 and 100.6 MHz for $^1H$ and $^{13}C$ experiments, respectively, equipped with a 5 mm broadband probe and Bo gradients. All spectra were recorded using 9 mg of substance dissolved in 0.7 mL of $CDCl_3$. Chemical shifts in ppm are given relative to TMS. The $^1H$-$^1H$ shift correlated two dimensional (COSY) spectra are obtained using the COSY 90 pulse sequence. Reference is made to Picardo, M.; Passi, S.; Sirlanni, M. C.; Fiorilli, M.; Russo, G. D.; Cortesi, E.; Barile, G.; Breathnach, A. S.; Nazzaro-Porro, M., *Biochem. Pharmacol.* (1985), 34, 1653.

The type of carbon is defined by 2 experiments 1D (DEPT 90 and 135). The one-bond $^1H$-$^{13}C$ chemical shift correlation (HMQC) spectra had been obtained according to the Bax sequence using Bo gradient pulses for the selection of $^1H$ coupled to $^{13}C$ carbons. Reference is made to Breathnach, A. S. *Med. Hypoth.* (1999), 52, 221.

The $^1H$ detected heteronuclear multiple bond correlation (HMBC) spectra were recorded using the pulse sequence proposed by Bax and Summers involving a low pass Jn filter (3.8 ms) and a delay to observe the long-range coupling (60 ms) as in the HMQC experiment, $B_o$ gradient pulses were applied to select $^1H$ coupled to $^{13}C$ nuclei. Gradient selected NOESY spectra were acquired with the NOESYGPPH Bruker pulse program.

Hereafter, the synthesis and the features of three compounds according to the present invention are detailed.

A) bis[O-(14-benzoylaconine-8-yl)]-pimelate (PDD)

Synthesis of the Compound:

Aconitine (200 mg, 0.30 mmol) and pimelic acid (24 mg, 0.15 mmol) in DMF (5 ml) was stirred up during 7 hours at 80° C. The mixture is agitated during a night at room temperature. The solvent is then evaporated under reduced pressure at a temperature lower than 70° C. The oily residue is purified by semi-preparative high pressure liquid chromatography.

NMR Features of the Obtained Compound:

White powder: $^1H$ NMR spectrum (400.13 MHz, $CDCl_3$) showed δ: 8.1 (d, 4H, J=7.6, H-2'/H-6'), 7.71 (t, 2H, J=7.4, H-4'), 7.58 (t, 4H, J=7.6, H-3'/H-5'), 5.04 (d, 2H, J=4.4, H-14), 4.63 (d, 2H, J=5.2, H-15), 4.44 (br s, 2H, H-3), 4.27 (br d, 2H, H-6), 3.92 ($m^a$, 2H, H-19b), 3.95 (s, 6H, 16-$OCH_3$), 3.67 (s, 2H, H-18$b^a$), 3.64 (m, 2H, H-1), 3.53 (s, 6H, 1-$OCH_3$), 3.48 (s, 2H, H-17), 3.47 (s, 6H, 18-$OCH_3$), 3.41 (s, 2H, 18$a^a$), 3.39 (br d, 2H, H-16), 3.36 (s, 6H, 6-$OCH_3$), 3.31 ($m^a$, 2H, H-19a), 3.33 ($m^a$, 4H, N—$CH_2$—$CH_3$), 3.08 ($m^a$, 2H, H-9), 3.06 (s, 2H, H-5), 2.74 (br d, 2H, H-7), 2.58 (br s, 2H, H-2b), 2.51 (br d, 2H, H-12b), 2.49 ($m^a$, 2H, H-10), 2.07 (d, 2H, J=10, H-12a), 1.87 (m, 2H, 8-$CO_2$—($CH_2$)1"b, 8-$CO_2$—($CH_2$)$_6$"b), 1.60 (m, 10H, 8-$CO_2$—($CH_2$)1"a, 8-$CO_2$—($CH_2$)$_5$"a, N—$CH_2$—$CH_3$, H-2$a^a$), 1.12 (m, 2H, 8-$CO_2$—($CH_2$)$_2$"b, 8-$CO_2$—($CH_2$)$_4$"b), 0.95 (m, 2H, 8-$CO_2$—($CH_2$)$_2$"a, 8-$CO_2$—($CH_2$)$_4$"a), 0.72 (quint, 2H, J=7.2, 8-$CO_2$—($CH_2$)$_3$"). $^{13}C$ NMR ($CDCl_3$) δ: 174.9 (8-COO, 8-COO"), 165.76 (C-7'), 133.8 (C-4'), 129.9 (C-2'/C-6'), 129.5 (C-1'), 129 (C3'/C-5'), 90 (C-16), 89.98 (C-8), 82.48 (C-6), 79.83 (C-1), 78.12 (C-15), 78.45 (C-14), 75.79 (C-18), 74.02 (C-13), 69.9 (C-3), 63.12 (C-17), 62.01 (16-$OCH_3$), 59.3 (18-$OCH_3$), 59.05 (6-$OCH_3$), 55.36 (1-$OCH_3$), 50.63 (C-19), 50.42 (C-11), 50.38 (N—$CH_2$—$CH_3$), 45.0 (C-5), 43.42 (C-4), 43.47 (C-9), 41.91 (C-7), 40.09 (C-10), 35.01 (C-12), 34.27 (C-1", C-5"), 29.49 (C-2", C-4"), 28.02 (C-2), 23.86 (C-3"), 10; 99 (N—$CH_2$—$CH_3$).

B) bis[O-(14-benzoylaconine-8-yl)]-suberate (SDD)

Synthesis of the Compound:

Aconitine (200 mg, 0.30 mmol) and suberic acid (26 mg, 0.15 mmol) in DMF (5 mL) was stirred up during 7 hours at 80° C. The mixture is agitated during a night at room temperature. The solvent is then evaporated under reduced pressure at a temperature lower than 70° C. The oily residue is purified by semi-preparative high pressure liquid chromatography.

Features of the Obtained Compound:

White powder: $^1H$ NMR spectrum (400.13 MHz, $CDCl_3$) showed δ: 8.00 (d, 4H, J=7.8, H-2'/H-6'), 7.58 (t, 2H, J=7.32, H-4'), 7.46 (t, 4H, J=7.66, H-3'/H-5'), 5.04 (d, 2H, J=4.9, H-14), 4.64 (d, 2H, J=5.36, H-15), 4.43 (br s, 2H, H-3), 4.28 (d, 2H, J=6.1, H-6), 3.97 (d, 2H, J=12.96, H-19b), 3.94 (s, 6H, 16-$OCH_3$), 3.67 (s, 2H, H-18ba), 3.64 (m, 2H, H-1), 3.53 (s, 6H, 1-$OCH_3$), 3.47 (s, 2H, H-17), 3.43 (s, 6H, 18-$OCH_3$), 3.41 (s, 2H, 18aa), 3.39 (d, 2H, J=5.4, H-16), 3.36 (s, 6H, 6-$OCH_3$), 3.31 (d, 2H, J=12.96, H-19a), 3.30 ($m^a$, 4H, N—$CH_2$—$CH_3$), 3.10 (m, 2H, H-9), 3.07 (s, 2H, H-5), 2.74 (d, 2H, J=6.1, H-7), 2.58 (br s, 2H, H-2b), 2.51 (br d, 2H, H-12b), 2.49 (m, 2H, H-10), 2.07 (d, 2H, J=9.9, H-12a), 1.94 (m, 2H, 8-CO2-(CH2)1"b, 8-CO2-(CH2)6"b), 1.63 (m, 2H, 8-CO2-(CH2)1"a, 8-CO2-(CH2)6"a), 1.60 (t, 6H, J=6.98, N—$CH_2$—$CH_3$), 1.56 (br d, 2H, H-2aa), 1.24 (m, 2H, 8-CO2-(CH2)2"b, 8-CO2-(CH2)5"b), 1.09 (m, 2H, 8-CO2-(CH2)2"a, 8-CO2-(CH2)5"a), 0.83 (m, 4H, 8-CO2-(CH2)3", 8-CO2-(CH2)4"). $^{13}C$ NMR (CDCl3) δ: 175.1 (8-COO, 8-COO"), 165.8 (C-7'), 133.8 (C-4'), 129.9 (C-2'/C-6'), 129.5 (C-1'), 129 (C3'/C-5'), 90 (C-16), 89.97 (C-8), 82.51 (C-6), 79.82 (C-1), 78.82 (C-15), 78.40 (C-14), 75.75 (C-18), 74.01 (C-13), 70 (C-3), 63.13 (C-17), 61.95 (16-$OCH_3$), 59.26 (18-$OCH_3$), 59.01 (6-$OCH_3$), 55.29 (1-$OCH_3$), 50.64 (C-19), 50.51 (C-11), 50.28 (N—$CH_2$—$CH_3$), 45.0 (C-5), 43.43 (C-4), 43.40 (C-9), 41.87 (C-7), 40.06 (C-10), 35.0 (C-12), 34.49 (C-1", C-6"), 29.50 (C-2), 28.54 (C-3", C-4"), 24.05 (C-2", C-5"), 10; 94 (N—$CH_2$—$CH_3$).

Furthermore, an ESI spectrum of bis[O-(14-benzoylaconine-8-yl)]-suberate has been carried out. Two peaks are observed on this spectrum: a major one at m/z 673.3 which corresponds to a doubly charged mass and a minor one at m/z 1345.7 which corresponds to a mono charged peak, this spectrum enables us to confirm.

High resolution mass measurements were also performed to confirm the formula of the synthesized compound. The experimental mass obtained on the mono-charged peak is 1345.6829. The theoretical mass for the formula $C_{72}H_{101}N_2O_{22}$ is 1345.6840 (high resolution mass).

$MS^2$ experiments were also performed. These measurements were done with the mono charged and the doubly charged peaks. The fragmentation of m/z 1346.7 (mono charged peak) produced a major fragmentation peak at m/z 760 which corresponds to the loss of one of the aconitine unit. Fragmentation of m/z 673 (doubly charged peak) produced more fragments which correspond to the mechanism of fragmentation of the aconitine unit.

C) bis[O-(14-benzoylaconine-8-yl)]azelate (ADD)

Synthesis of the Compound:
Aconitine (200 mg, 0.30 mmol) and azelaic acid (29 mg, 0.15 mmol) in DMF (5 mL) was stirred up during 7 hours at 80° C. The mixture is agitated during a night at room temperature. The solvent is then evaporated under reduced pressure at a temperature lower than 70° C. The oily residue is purified by semi-preparative high pressure liquid chromatography.

Features of the Obtained Compound:
White powder: $^1$H NMR spectrum (400.13 MHz, $CDCL_3$) showed δ: 8.03 (d, 4H, J=7.2, H-2'/H-6'), 7.56 (t, 2H, J=7.4, H-4'), 7.45 (t, 4H, J=7.2, H-3'/H-5'), 5.09 (d, 2H, J=5, H-14), 4.51 (d, 2H, J=5.2, H-15), 4.30 (br s, 2H, H-3), 4.12 (d, 2H, J=6.1, H-6), 4.06 (d, 2H, J=11.91, H-19b), 3.79 (s, 6H, 16-$OCH_3$), 3.52 (s, 2H, H-18b$^{a)}$, 3.47 (m, 2H, H-1), 3.36 (s, 6H, 1-$OCH_3$), 3.29 (s, 2H, H-17), 3.27 (s, 6H, 18-$OCH_3$), 3.24 (s, 2H, 18a$^a$), 3.22 (br s, 2H, H-16), 3.19 (s, 6H, 6-$OCH_3$), 3.11 (d, 2H, J=11.9, H-19a), 3.16 (m, 4H, N—$CH_2$—$CH_3$), 2.90 (m, 2H, H-9), 2.86 (s, 2H, H-5), 2.55 (d, 2H, J=6.1, H-7), 2.34 (br s, 2H, H-2b), 2.28 (br d, 2H, H-12b), 2.24 (m, 2H, H-10), 2.02 (br d, 2H, H-12a), 1.82 (m, 2H, 8-$CO_2$—($CH_2$)1"b, 8-$CO_2$—($CH_2$)7"b), 1.50 (m, 2H, 8-$CO_2$—($CH_2$)1"a, 8-$CO_2$—($CH_2$)7"a), 1.42 (t, 6H, J=7.01, N—$CH_2$—$CH_3$), 1.35 (br s, 2H, H-2a$^a$), 1.13 (m, 4H, 8-$CO_2$—($CH_2$)2"b, 8-$CO_2$—($CH_2$)3"b, 8-$CO_2$—($CH_2$)5"b, 8-$CO_2$—($CH_2$)6"b), 1.04 (m, 4H, 8-$CO_2$—($CH_2$)2"a, 8-$CO_2$—($CH_2$)3"a, 8-$CO_2$—($CH_2$)5"a, 8-$CO_2$—($CH_2$)6"a), 0.87 (m, 2H, 8-$CO_2$—($CH_2$)4"). $^{13}$C NMR ($CDCl_3$) δ: 175.1 (8-COO, 8-COO"), 166 (C-7'), 134 (C-4'), 130 (C-2'/C-6'), 129.7 (C-1'), 129.3 (C3'/C-5'), 90.3 (C-16), 90.1 (C-8), 82.9 (C-6), 80.1 (C-1), 79.0 (C-15), 78.7 (C-14), 76.0 (C-18), 74.3 (C-13), 70.3 (C-3), 63.4 (C-17), 60.9 (16-$OCH_3$), 59.5 (18-$OCH_3$), 59.06 (6-$OCH_3$), 55.6 (1-$OCH_3$), 50.7 (C-19), 50.51 (C-11), 50.50 (N—$CH_2$—$CH_3$), 45.4 (C-5), 43.7 (C-4), 43.40 (C-9), 41.9 (C-7), 40.5 (C-10), 35.3 (C-12), 34.49 (C-1", C-7"), 28.8 (C-2", C-6"), 26.54 (C-3", C-5"), 24.05 (C-4"), 11 (N—$CH_2$—$CH_3$).

Evaluation of bis[O-(14-benzoylaconine-8-yl)]azelate (ADD)-suberate (SDD) and -pimelate (PDD) alkaloids In vitro Cytotoxicity Test Against Human Tumour Cell Lines
Materials and Methods.

Human tumour cell lines A549 (lung cancer), HCT-15 (colon cancer) and MCF-7 (breast cancer) have been obtained from the Developmental Therapeutics Program of the National Cancer Institute (Rockville, Md., USA). Cells were routinely grown with RPMI 1640 medium supplemented with 10% foetal calf serum, both obtained from Biochrom AG (Berlin, Germany). They were grown on Petri dishes (Nunc, Denmark) at 37° C. in a humidified atmosphere containing 5% $CO_2$. Cells were replicated every 4 days and the medium changed once in-between.

Cytotoxicity has been evaluated on exponentially growing cells grown for 24 h in presence of the compounds to be tested. Briefly, 4000 cells were seeded in 96-well plates with 200 μL of complete medium; 24 hours later the medium was supplemented with a series of different concentrations of compounds and the contact maintained for 24 h. Compounds were dissolved in pure water and sterilised using polycarbonate membrane filters of 0.22 μm (Millipore, Molsheim, France). The cells were then allowed to re-grow for 48 hours; viable and metabolically active cells were quantitatively estimated by coloration with the MTT dye (1-(4,5-dimethylthyazol-2-yl)-3,5-diphenylformazan), Sigma-Aldrich Chimie, Saint-Quentin-Fallavier, France). The amount of substance allowing a 50% decrease in cell numbers is indicative of the cytotoxicity and represents the $IC_{50}$ of compound.

The following table 1 shows the cytotoxicity effects of the three bis[O-(14-benzoylaconine-8-yl)]-azelate (ADD), bis [O-(14-benzoylaconine-8-yl)]-suberate (SDD) and bis[O-(14-benzoylaconine-8-yl)]-pimelate (PDD).

More precisely, table 1 summarizes the $IC_{50}$ values (μM) of:
bis[O-(14-benzoylaconine-8-yl)]-azelate (ADD),
bis[O-(14-benzoylaconine-8-yl)]-suberate (SDD),
bis[O-(14-benzoylaconine-8-yl)]-pimelate (PDD), and
8-O-azeloyl-14-benzoylaconine (Comparison 1), and
four major anticancer drugs (Comparison 2), as they appear in the data base of the Development Therapeutic Program of the National Cancer Institute, and which are:
fluorouracil (i.e. 5-FU),
cisplatin,
etoposide,
mephalan
tested on:
A549,
HCT-15, and
MCF-7 human tumour cell lines,

TABLE 1

$IC_{50}$ values (μM) of several compounds tested on A459, HCT-15 and MCF-7 human tumour cell lines

| | | The IC50 values of the substances, in μM | | |
|---|---|---|---|---|
| | | A549 | HCT-15 | MCF-7 |
| | ADD | 19.13 | 22 | 15.45 |
| | SDD | 18.7 | 3.7 | 3.7 |
| | PDD | 3.76 | 3.76 | 7.5 |
| Comparison 1 | 8-O-azeloyl-14-benzoylaconine | 16.8 | 19.4 | 10.3 |

TABLE 1-continued

IC$_{50}$ values (µM) of several compounds tested on A459,
HCT-15 and MCF-7 human tumour cell lines

| | | The IC50 values of the substances, in µM | | |
|---|---|---|---|---|
| | | A549 | HCT-15 | MCF-7 |
| Comparison 2 | 5-FU | 2.11 | 5.69 | 1.75 |
| | cisplatin | 3.08 | 7.21 | 3.01 |
| | etoposide | 3.61 | 17.6 | 5.73 |
| | mephalan | 28.7 | 39.4 | 11.1 |

It can be observed from the table 1 that all the compounds according to the invention show inhibitory effects. The best results were found for the two SDD and PDD with values comparable with those of the four major anticancer drugs (comparison 2). On the other hand, ADD showed inhibitory effect quite similar as those for corresponding 8-O-azeloyl-14-benzoylaconine.

Hereafter, studies, which were carried out on the most potent bis[O-(14-benzoylaconine-8-yl)]-suberate (SDD) of these three compounds according to the invention, are described.

Partition Coefficients: log D (pH 7.4) of SDD

Partition coefficients between water/octanol allow evaluating the water/lipo-solubility of the compound. This plays a major role in determination of pharmacokinetic parameters such as penetration of various biologic barriers and distribution within living organisms.

The relative log D (pH 7.4) in this study was assessed by the micro HPLC method which is disclosed in A microscale HPLC method for the evaluation of octanol-water partition coefficients in a series of new 2-amino-2oxazolines Pehourcq, F.; Thomas, J.; Jarry, C., J. Liq. Chromatogr. Relat. Technol. (2000), 23, 443-453.

These determinations were performed with a chromatographic apparatus (Spectra Series, San Jose, USA). A reversed phase column was used: a Stability RP18 (4.6×150 mm; 5 µm particle size) with a mobile phase consisting of acetonitrile (+1‰ trifluoroacetic acid)–water (+1‰ trifluoroacetic acid) (40:60 v/v).

The compound was partitioned between n-octanol (HPLC grade) and phosphate buffer (pH=7.4). Octanol was presatured with buffer, and conversely. An amount of 1 mg of the compound was dissolved in an adequate volume of methanol in order to achieve 1 mg/mL stock solutions. Then, an appropriate aliquot of this methanolic solution was dissolved in buffer to obtain final concentration of 100 µg/mL. Under the above described chromatographic conditions, 20 µL of this aqueous phase was injected into the chromatograph, leading to the determination of a peak area before partitioning (W0).

In screw-capped tubes, 2000 µL of the aqueous phase ($V_{aq}$) was then added to 10 µL of n-octanol ($V_{oct}$) at pH=7.4. The mixture was shaken by mechanical rotation during 30 min. Centrifugation was achieved at 3000 rpm in 15 min. An amount of 20 µL of the lower phase was injected into the chromatograph column. This led to the determination of a peak area after partitioning ($W_1$). Log D was calculated from the formula: log D=log [$(W_0-W_1)V_{aq}/W_1V_{oct}$].

Concerning the compound SDD, a value of 2.86 of log D (pH 7.4) has been found, which corresponds to a relatively high liposolubility, favorable to a trans-membrane penetration of various biologic barriers and distribution within living organisms, according to the following publication: Lipinski, C. A.; Lombardo, F.; Dominy, B. W.; Feeney, P. J., Adv. Drug Delivery Rev. (1997), 23, 3-25.

Experimental and Computational approaches to estimate solubility and permeability in drug discovery and development setting, in which an empirical scale of liposolubility is disclosed.

Effect of bis[O-(14-benzoylaconine-8-yl)]-suberate
(SDD) on cell cycle arrest of different tumour cell
lines Method.

$10^6$ Cells of A549, HCT-15 and MCF-7 cell lines have been seeded in Petri dishes with RPMI-1640 medium. 24 h later, SDD has been dissolved in water at a concentration of 20 µM and was directly added to the culture medium. Contact was maintained for 72 h. Then, cells have been detached by trypsinization, collected and rinsed by PBS and counted on hemocytometer. Cells were centrifuged for 5 min at 1500 rpm, then resuspended in a defined volume of PBS to obtain $2.5 \times 10^6$ cell/mL. 100 µL of cell suspension was digested to nuclei by trypsin for 10 min. Then, a solution containing trypsin inhibitor and RNAse was added to cell suspension and left for 10 min. Finally, cells were stained by propidium iodide and were analysed by flow-cytometry apparatus. Distribution of cells among the different phases of the cycle was determined by the procedure disclosed in: A detergent-trypsin method for preparation of nuclei for flow cytometric DNA analysis. Vindelov, L.; Christensen, I.; Nissen, N.; Cytometry (1983), 3, 323-327.

The following table 2 summarizes the results obtained

G0G1: cell in the phase of G0G1

G2M: cells in the phase of G2M

S: cells in the phase of DNA synthesis

Sub G1: apoptotic cells

SUP G2M: diploidic cells

TABLE 2

Influence of SDD on tumour cell cycle arrest
percentages of total cell population.

| Tumour cell lines | | Control (untreated cells) | SDD (20 µM) |
|---|---|---|---|
| A549 | ALL % | 100 | 100 |
| | G0G1 % | 76.28 | 53.04 |
| | G2M % | 9.15 | 16.42 |
| | S % | 12.42 | 25.49 |
| | SubG1 % | 1.74 | 3.34 |
| | SUP G2M % | 0.72 | 2.09 |
| HCT-15 | ALL % | 100 | 100 |
| | G0G1 % | 69.83 | 30.67 |
| | G2M % | 11.94 | 15.72 |
| | S % | 15.19 | 26.35 |
| | SubG1 % | 2.29 | 23.65 |
| | SUP G2M % | 0.81 | 2.59 |
| MCF-7 | ALL % | 100 | 100 |
| | G0G1 % | 66.01 | 58.73 |
| | G2M % | 13.51 | 16.96 |
| | S % | 16.56 | 21.44 |
| | SubG1 % | 2.96 | 2.05 |
| | SUP G2M % | 0.87 | 1.72 |

The following table 3 summarizes the percentages of survival cells in different cell cycles.

TABLE 3

Percentage of survival cells in different cell cycles

|  | A549 | | HCT-15 | | MCF-7 | |
| --- | --- | --- | --- | --- | --- | --- |
|  | Control | SDD | Control | SDD | Control | SDD |
| G0G1 % | 77.96 | 55.86 | 72.01 | 42.16 | 68.7 | 60.46 |
| G2M % | 9.35 | 17.29 | 21.32 | 21.61 | 14.07 | 17.46 |
| S % | 12.7 | 26.84 | 15.67 | 36.23 | 17.23 | 22.08 |

Results

As the table 2 shows, SDD, at the dose of 20 μM, it led to a significant accumulation of A549 and HCT-15 cells and moderate accumulation of MCF-7 cells in the G2M and S phases, which is characteristic of cell cycle arrest at these stages of development. The numbers of apoptotic cells (Sub G1) was significantly increased in the test with HCT-15 cell lines.

It is important to notice that the number of cells in the G2M phase increased respectively by 85% and 75% in A549 and HCT-15 cell lines, and the number of cells arrested at S phase increased by more than 100% in both cell types as compared to control.

Upon SDD treatment similar trend of accumulation in G2M and S phase were noticed in MCF-7 cells but to a lower degree. The effect on cell cycle was not correlated with the cytotoxicity of SDD: A549 cell distribution in the cell cycle was altered at a SDD concentration close to $IC_{50}$, whereas MCF-7 cell distribution in the cycle was not altered at a SDD concentration 5 times higher than $IC_{50}$. This makes us to suppose multiple action mechanisms, not only limited to inhibition of DNA synthesis and block of G2M phase.

Study of the Effect of SDD on Topoisomerase I Cleavage Activity.

DNA topoisomerase 1 (i.e. Top 1) is an essential nuclear enzyme involved in the regulation of DNA topology associated with most DNA transactions, including replication, transcription recombination and chromatin remodelling. Its role is to introduce transient single strand breaks in duplex DNA via the formation of a covalent bond between the 3'-phosphate of the cleaved strand and enzyme. Within the covalent Top 1-DNA complex, rotation of the broken strand around the uncleaved strand results in DNA supercoil relaxation. DNA continuity is then restored by Top 1 catalysed religation of the 5'-hydroxyl termini. Top 1 poison, such as Camptothecin (CPT) stabilizes the Top 1-DNA complex, and consequently, inhibit DNA religation.

The influence of SDD has been studied at various concentrations on Top 1 cleavage activity in comparison with Camptothecin.

The method consists in an incubation of 3'-labeled oligonucleotides with enzyme Top1, or Top 1+CPT or Top 1-SDD. Top 1 forms covalent bind with the 3'-terminus of a DNA single strand beak and then religates DNA, which is revealed as a single band, Camptothecin, as a positive control stabilize the complex Top1-DNA, inhibiting religation of DNA, thus, is revealed as double band.

Method.

Oligonucleotide Labelling

3'-end labelling of the scissile strand was performed as described previously in the publication: Conversion of topoisomerase I cleavage complexes on the leading strand of ribosomal DNA into 5'-phosphorylated DNA double-strand breaks by replication runoff. Pommier, Y.; Jenkins, J.; Kohlhagen, G.; and Leteurtre, F.; Mutat. Res. (1995), 337, 135-145.

Thus, 10 pmol of deoxynucleotidyltransferase was incubated in labelling buffer (100 mM potassium cacodylate, pH 7.2, 2 mM $CaCl_2$, 200 μM DTT) for 1 h at 37° C.

The reaction mixture was passed through a G-25 Sephadex spin column by centrifugation at 1000 g for 5 min to remove the excess of unincorporated nucleotide.

The 3'-labeled oligonucleotide was mixed with the same amount of unlabeled complementary strand in annealing buffer (i.e. 10 mM Tris-HCl, pH 7.8, 100 mM $Na_2EDTA$) and annealed by heating the reaction mixture for 5 min at 95° C. followed by slow cool down at room temperature.

Top1-catalysed Cleavage Assays

Top1-catalysed cleavage assays were performed using either full duplex oligonucleotides or partially double-stranded oligonucleotides, referred to as suicide substrates.

For each reaction, 20 fmol of 3'-labeled substrate at a concentration of 10 μM was incubated with 0.2 μmol of purified human recombinant Top 1 in a buffer containing 10 mM Tris-HCl, pH 7.5, 50 mM KCl, 5 mM $MgCl_2$, 0.1 mM $Na_2EDTA$, 15 μg of bovine serum albumin, 0.2 μM DTT, and 10 μM CPT with or without SDD for 15 min at room temperature.

Reactions were stopped by the addition of 0.5% SDS, loading buffer (i.e. 80% formamide, 10 μM NaOH, 1 μM $Na_2EDTA$, 0.1% xylencyanol, 0.1% bromphenol blue) in a proportion of (3:1) and the samples were resolved in 16 or 20% acrylamide DNA sequencing gels containing 7 M urea.

Imaging and quantification of the cleavage products were performed using a Typhoon Phosphorimager (Amersham Biosciences) as described in Inhibition of Topoisomerase I cleavage activity by thiol-reactive compounds. Montaudon, D.; Palle, K.; Rivory, L.; Robert, J.; Douat-Casassus, C.; Quideau S.; Bjornsti M.; Pourquier P; J. Biol. Chem. (2007), 282, 14403-14412.

Results

SDD used in four different concentrations: 1, 10, 100 and 1000 μM has revealed no Top 1 inhibitory activity compared with camptothecin.

Evaluation of the Effect of SDD on Catalytic Activity of Topoisomerase II.

It is generally admitted that nuclear enzyme DNA topoisomerase II (Topo II) is the common target for a variety of anticancer drugs, including anthracyclines, acridines, epipodophyllotoxines and ellipticines. Despite the fact that all these drugs induce formation and stabilization of a ternary complex DNA-drug-Topo II, the domains and mechanisms of specific binds seems not to be the same for different chemical groups, which determine the pharmacologic characteristics of drugs such as efficacy and resistance.

Test for revelation of the possible inhibitory effect of SDD on Topo II catalytic activity has been undertaken by decatenation of a catenated DNA substrate originating from *Trypanosoma kinetoplasts* (kDNA, TopoGen) into relaxed DNA forms.

Method.

The following standard reaction mixture contained 40 mM Tris/HCl pH 7.4, 10 mM $MgCl_2$, 0.5 mM dithiothreitol, 1 mM ATP and 0.02 g/ml kDNA has been carried out.

The reaction was initiated by the addition of 0.35 M NaCl nuclear extract and stopped after 20 min incubation at 37° C. by adding a denaturating solution containing 30% glycerol, 1% SDS, 0.5 mg/ml bromphenol blue.

The samples were then electrophoresed on a 1% agarose gel in 40 mM Tris/acetic acid, pH 8.0 containing 2 mM EDTA and 0.1 µg/ml ethidium bromide, for 45 min at 80V.

A positive control for decatenation was a decatenated kDNA marker obtained from TopoGen, containing a mixture of two species of relaxed DNA, open circular DNA and covalently closed circular DNA. Catenated DNA does not enter the gel, while decatenated DNA circles do enter the gel and migrate.

DNA was visualized under UV light and the various DNA forms were quantified by densitometric scanning using the device described above.

Etoposide was used as positive control, as it is described in the following publication: Differential stabilisation of topoisomerase-II-DNA cleavable complexes doxorubicine and etoposide in doxorubicin-resistant rat glioblastoma cells. Montaudon, D.; Pourquier, P.; Denois, F.; De Tinguy-Moreaud, E.; Lagarde, P.; Robert, J.; Eur., *J. Biochem.* (1997), 245, 307-315.

Results

SDD used in concentrations 1, 10, 100 and 1000 µM has caused relatively moderate inhibition of Topo II activity compared to etoposide in dose independent manner. Thus, there is insignificant inhibition of the Topo II activity, but, it does not depend on the concentrations of SDD.

Acute Toxicity Determination for SDD ($LD_{50}$)

The study has been performed to assess the acute systemic toxicity of SDD in the mouse preliminary test.

The SDD was administered, by intravenous route:

in a first step to 1 female Swiss mouse at the single dose of 95 mg/kg b.w., in a second step to 1 female Swiss mouse at the single dose of 60 mg/kg b.w., in a third step to 1 female Swiss mouse at the single dose of 55 mg/kg b.w., and in a fourth step to a group of 2 female Swiss mice at the single dose of 50 mg/kg b.w.

It was noted the death of the animal treated at 95 mg/kg b.w., immediately after the test item administration.

It was noted the death of the animal treated at 60 mg/kg b.w., 3 hours after the test item administration.

The mortality was preceded by a decrease of the spontaneous activity associated with a decrease of Preyer's reflex, an absence of the righting reflex, a decrease of muscle tone and the eyes partly closed.

It was noted the death of the animal treated at 55 mg/kg b.w., 24 hours after the test item administration. The mortality was preceded by a decrease of the spontaneous activity associated with a decrease of the righting reflex.

No mortality occurred in the animals treated at 50 mg/kg b.w.

It was registered, 1 hour after the test item administration, a decrease of the spontaneous activity (2/2) (i.e. 2 mice out of 2 mice) associated with a decrease of the righting reflex (1/2). The animals recovered a normal activity the second day of the test.

It was noted an oedema at the level of the tails of the mice between the first day and the fourteenth day.

The body weight evolution of the animals remained normal throughout the study. The macroscopical examination of the animals treated at 50 mg/kg at the end of the study did not reveal any treatment-related changes.

Main Test

The SDD was administered by intravenous route at the dose of 50 mg/kg body weight to a group of 5 female Swiss mice. The experimental protocol was established from the International standard NF EN ISO 10993-11 concerning biological evaluation of medical devices: "Tests for systemic toxicity".

No mortality occurred during the study. It was registered in the treated animals, 1 hour after the test item administration, a decrease of the spontaneous activity (5/5) associated with a decrease of the righting reflex (2/5) and the eyes partly closed (2/5). The animals recovered normal activity the 2nd day of the test.

It was noted an oedema at the level of the tails of mice between the first day and the fourteenth day. The body weight evolution of animals remained normal throughout the study. The macroscopical examination of animals treated at 50 mg/kg at the end of the study revealed only necrosis at the level of the tail (3/5).

Conclusion

In conclusion, the mouse $LD_{50}$ for SDD is found above 50 mg/kg of body weight, when administered by intravenous route.

The invention claimed is:

1. Compound of the general structure (I)

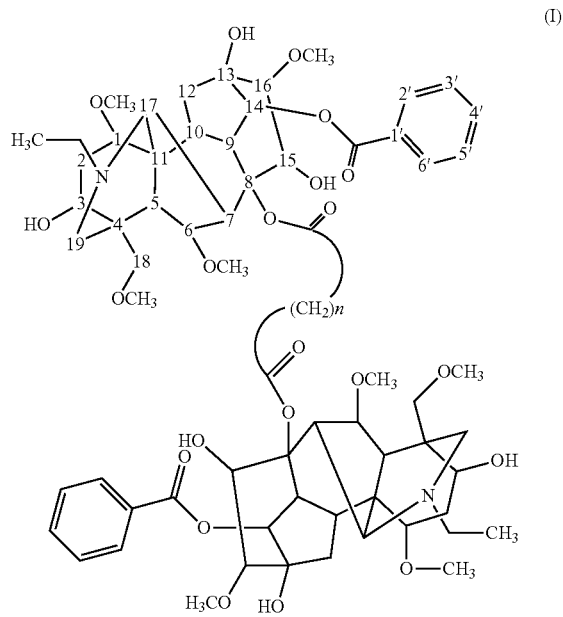

wherein n is an integer comprised between 0 and 10.

2. The compound according to claim 1 wherein n is comprised between 4 and 8.

3. The compound according to claim 1 wherein n is equal to 5 or 6 or 7.

4. The compound according to claim 1 which is the bis[O-(14-benzoylaconine-8-yl)]-suberate.

5. A method for the production of a compound having the general structure (I),

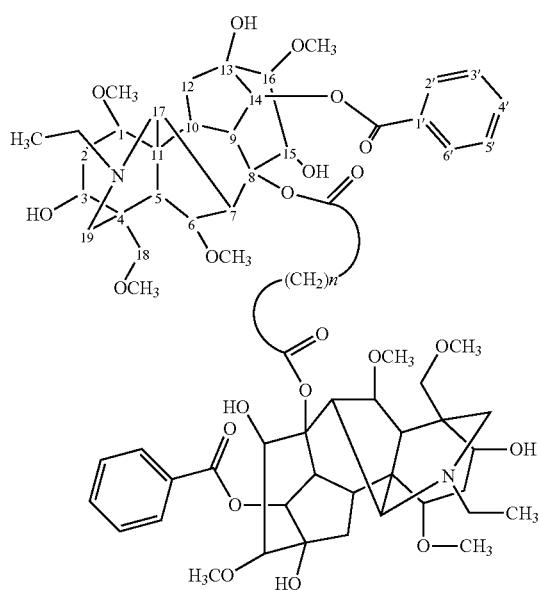 (I)

wherein n is an integer comprised between 0 and 10,
wherein said method comprises the following steps:
a) stirring aconitine with a dicarboxylic acid at a temperature equal or lower than 80° C. in a solvent such DMF,
b) agitating the obtained mixture at room temperature such that the reaction of transesterification is carried out,
c) evaporating the solvent under reduced pressure,
d) purification of the oily residue obtained at the end of the step c) to isolate the said compound (I).

6. The method according to claim 5 wherein the dicarboxylic acid has a number of carbon atoms comprised between 2 and 12.

7. The method according to claim 6 wherein the dicarboxylic acid is selected from the group consisting of pimelic acid, suberic acid and azelaic acid.

8. A pharmaceutical composition comprising a compound as defined in claim 1.

9. The pharmaceutical composition according to claim 8 which further comprises a suitable, pharmaceutically acceptable diluent or carrier substance.

10. A method for fabricating a medicament comprising fabricating the compound according to claim 1 into a medicament.

11. The compound according to claim 1 wherein n is an integer comprised between 3 and 10.

12. The method according to claim 5 wherein the dicarboxylic acid has a number of carbon atoms comprised between 5 and 12.

13. The method according to claim 5 wherein the dicarboxylic acid has a number of carbon atoms comprised between 6 and 10.

14. A method for treatment of a tumour in a subject in need thereof comprising administering to the subject a compound according to claim 1 in an amount effective to treat the tumour wherein the tumour is colon, lung or breast tumour.

15. A method for treatment of cancer in a subject in need thereof comprising administering to the subject a compound according to claim 1 in an effective amount, wherein the cancer is colon, lung, or breast cancer.

* * * * *